United States Patent [19]

Bodine

[11] Patent Number: 5,306,230
[45] Date of Patent: Apr. 26, 1994

[54] KNEE EXTENDING ORTHOTIC APPLIANCE

[75] Inventor: Robert C. Bodine, Mission Viejo, Calif.

[73] Assignee: Rob Bodine/Capra Research, Laguna Hills, Calif.

[21] Appl. No.: 950,809

[22] Filed: Sep. 23, 1992

[51] Int. Cl.$^5$ .............................................. A61F 3/00
[52] U.S. Cl. ...................................... 602/26; 602/16; 602/23
[58] Field of Search .................... 602/23, 26, 27, 25, 602/5, 16; 128/80 R, 80 L, 80 H; 623/39, 42, 46

[56] References Cited

U.S. PATENT DOCUMENTS

| | | | |
|---|---|---|---|
| 2,558,986 | 7/1951 | Seelert | 602/23 X |
| 2,573,866 | 11/1951 | Murphy | 602/23 X |
| 3,230,952 | 1/1966 | Terron | 602/23 X |
| 3,316,900 | 5/1967 | Young | 602/16 |
| 4,494,534 | 1/1985 | Hutson | 602/23 X |
| 4,508,111 | 4/1985 | Hepburn | 602/16 |
| 4,848,326 | 7/1989 | Lonardo | 602/26 |
| 5,121,742 | 6/1992 | Engen | 602/26 X |

OTHER PUBLICATIONS

"Innovation Sports Announces The K.M.D. Post-OP Brace, A Marriage of Cost and Control," Physical Therapy Products, Jan. 1992.
"The 'S-1' Support, The Lumbar Stabilizer," IEM Orthopedic Systems, Inc., Ravenna, Ohio.
Ultraflex Dynamic Splint System, Bio-Tech, Inc., Malvern, Pa.
VersaWrist, Smith & Nephew DonJoy, Inc., Carlsbad, Calif.
"New Lightweight Knee Brace For Global Instabilities Of The Knee", Smith & Nephew DonJoy, Inc., Carlsbad, Calif.
Ultraflex Dynamic Splint, Bio-Tec, Inc., Malvern, Pa. 17B70 OTTO BOCK System Positioning Joint, Otto Bock Orthopedic Industry, Inc., Minneapolis, Minn.
Knee ROM Splints from LMB, LMB Hand Rehab Products, Inc., San Luis Obispo, Calif.
Pacesetter Post-Op Knee Brace by Carapace Incorporated of Tulsa, Okla., a Lohmann Company.

*Primary Examiner*—Richard J. Apley
*Assistant Examiner*—Beverly A. Meindl

[57] ABSTRACT

Disclosed is a device for maintaining extension of the knee joints of comatose, debilitated or bedridden patients. The device generally includes one or more elongate struts positionable adjacent the knee and having a bendable hinge formed therein to permit volitional bending of the knee. Such hinge is biased to an extended position so as to hold the knee in such extended position when not volitionally bent. An upper leg engaging member serves to anchor the upper ends of the elongate strut members to the leg, above the knee. A lower leg engaging member serves to anchor the lower ends of the strut members to the lower leg, below the knee. The lower leg engaging member may comprise a foot and ankle splint device which extends beneath the plantar surface of the foot, and which is attachable to the foot, thereby serving to prevent upward or downward movement of the device and further thereby limiting the need for tightening the device around the upper and/or lower leg of the patient.

22 Claims, 3 Drawing Sheets

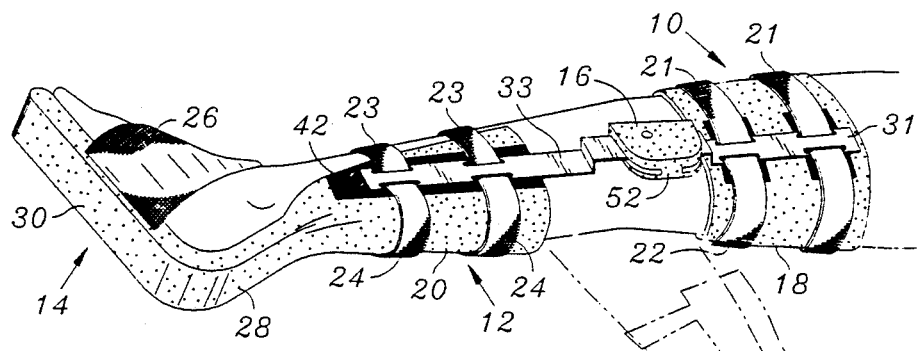
FIG. 1
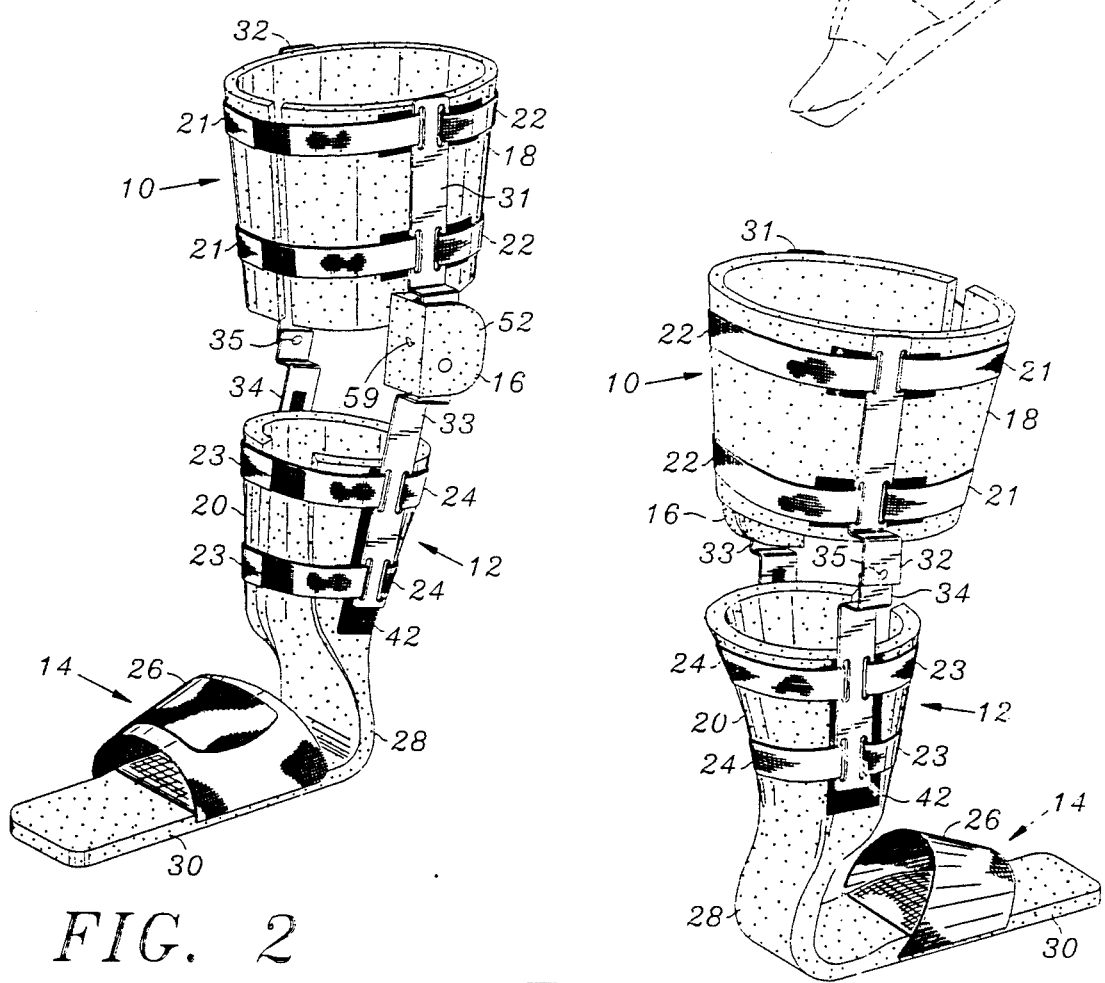
FIG. 2
FIG. 3

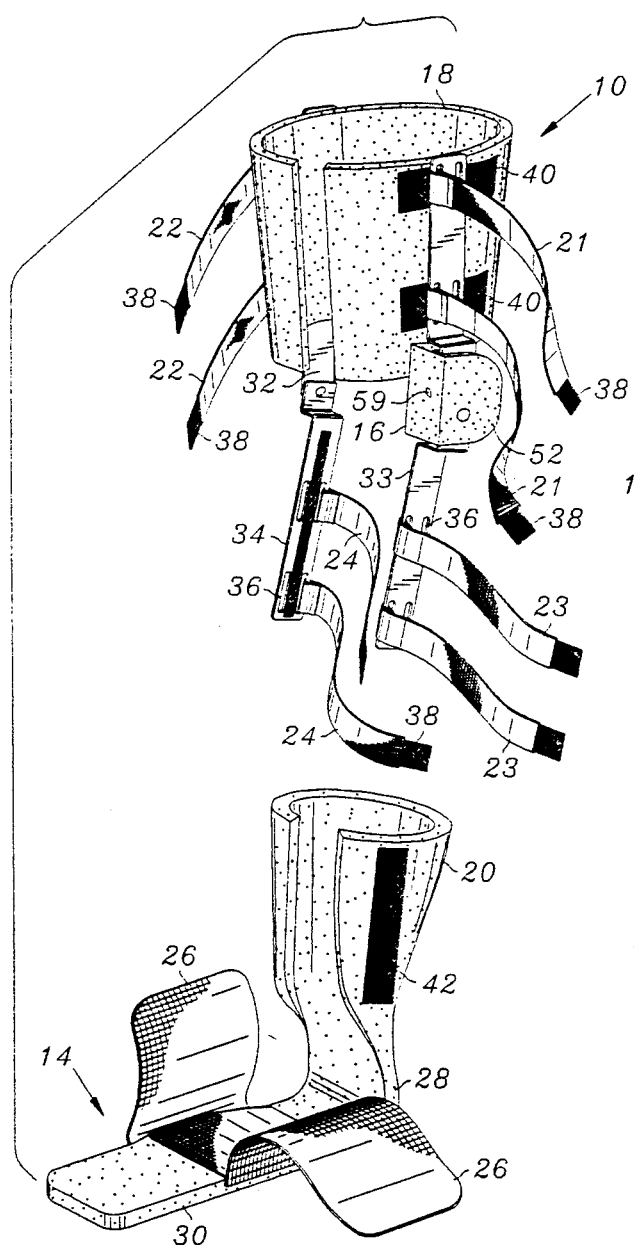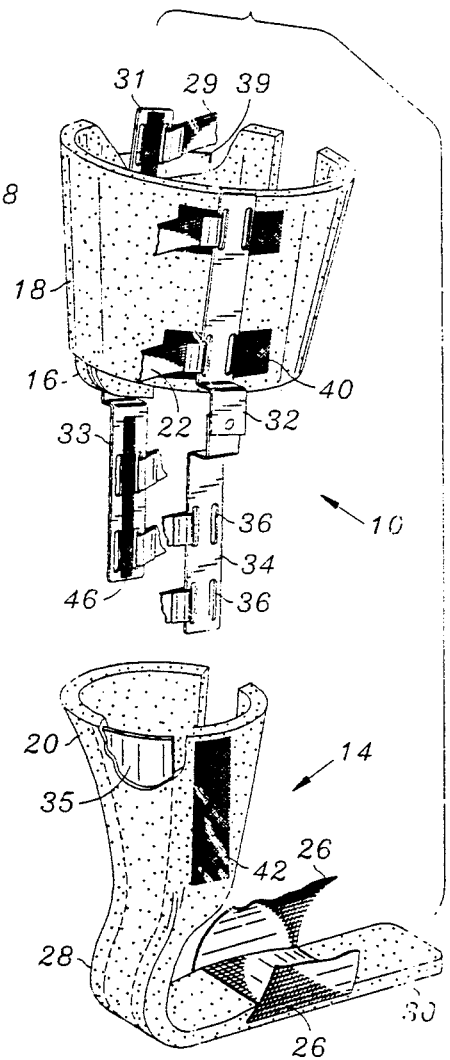

KNEE EXTENDING ORTHOTIC APPLIANCE

FIELD OF THE INVENTION

The present invention relates generally to medical devices and more particularly to an orthotic appliance which prevents or deters bending of the knee in bedridden patients, particularly those who have a tendency to assume a fetal-like position.

BACKGROUND OF THE INVENTION

Chronically ill, comatose, debilitated, elderly, or other bedridden patients frequently assume a contracted, fetal-like position wherein the legs are upwardly drawn and bent at the knees. Such upwardly drawn, knee-bent positioning of the legs over an extended period of time may result in atrophy of the leg muscles and/or other degenerative changes in the knee-joint-associated ligaments and tendons.

A number of orthotic appliances have heretofore been utilized to treat knee contracture by straightening the leg at the knee joint. One example of a knee-extension, orthotic appliance currently used in the art is the ProGlide ™ (L.M.B. Hand Rehab. Products, Inc., San Luis Obispo, Calif.). Such orthotic devices may also permit bending of the knee joint when desired. Such devices commonly comprise a spring-hinge attached to the leg at points immediately above and below the knee. Attachment is typically via leg surrounding members such as straps or the like. Such leg surrounding members or straps are typically secured around the leg by way of buckles, hook and loop attachment tabs (e.g., VELCRO ™) or other tightening hardware capable of holding the appliance in its desired position on the leg. The tension of the spring-hinge disposed proximate the knee joint thus urges the leg into an extended position.

One problem associated with these knee-extending orthotic devices of the prior art is the vertical (superior or inferior) shifting or slippage of the device despite reasonably secure tightening of the leg surrounding member or straps to the affixation points above and below the knee. In an effort to overcome the inherent tendency of such appliances to undergo vertical (e.g., superior or inferior) shifting or slippage, it is common to over tighten the leg surrounding members or straps about the patients thigh and calf.

Such tightening of the leg surrounding member or straps may be accomplished to a point where the appliance becomes generally uncomfortable for the patient and reduces circulation in the patient's leg or causes breakdown of sensitive skin. Decubitus ulcers may form if the device is worn for extended periods of time.

Similar devices have been commonly utilized as braces to provide support to a knee joint after an operation and/or injury. Although structurally similar, such braces typically lack a spring for urging the leg into an extended position. Thus, such devices are not optimal for use as leg extension maintaining orthotic appliances, since they do not allow the patient's knee to be volitionally bent when so desired. One example of such a leg brace is the K.M.D. Post-Op Brace manufactured by Innovation Sports, Inc. of Irvine, Calif.

Furthermore, chronically ill or bedridden patients tend to be susceptible to a condition known as "drop foot" or "foot drop" wherein the foot hangs in a plantar-flexed position due to neuro-muscular atrophy and/or lesions of the peroneal nerve. Drop foot and plantar flexion deformities have been known to develop in patients who spend substantial amounts of time lying in bed with the lower leg/ankle allowed to hang in a flaccid position. Traditionally, such plantar flexion deformities are known to develop in patients who have suffered strokes or other debilitating conditions. One mode of treating and/or preventing plantar flexion deformities of the ankle is to splint or immobilize the ankle of the flaccid leg such that a controlled degree of dorsiflexion of the foot will be maintained. Various splints and splint-like devices have been provided for accomplishing such immobilization of the ankle. Typically, the splints and splint-like devices have comprised generally L-shaped members, attachable to the lower leg and foot so as to hold the foot at or in an approximately 90-degree angle to the lower leg.

In addition to being useable for the prevention of and/or treatment of plantar flexion deformities in chronically ill or debilitated patients, foot splints and devices have also been used for various other therapeutic purposes including immobilization of the leg and foot to facilitate healing following traumatic injury and/or surgery.

One example of a splint device is that disclosed in U.S. Pat. No. 5,020,523 (Bodine), issued on Jun. 4, 1991, the entirety of which expressly incorporated herein by reference.

In view of the inherent deficiencies of the prior art, it is desirable to provide a knee-extending orthotic appliance need not be fastened so tightly around the leg as to cause discomfort or to, adversely affect circulation, and/or cause decubitus ulcers. It is also be desirable to provide a knee-extending orthopedic appliance having a removable foot orthosis component which may be used alone or in conjunction with the knee-extending component of the device to prevent degeneration changes in the lower leg, ankle and foot. (e.g., foot drop)

SUMMARY OF THE INVENTION

The present invention comprises an appliance which is affixable to the human leg to urge the knee joint to an extended, non-bent position so as to prevent atrophy or continued contracture of the knee joint in comatose, bedridden or debilitated patients.

In one embodiment, the appliance of the present invention comprises at least one elongate strut member positionable laterally and/or medially adjacent the knee, said strut member being bendable to permit volitional bending of the knee, and biased to urge the knee toward an extended non-bent position. Preferably, two strut members will be provided—a medial strut member positionable alongside the medial aspect of the knee and a lateral strut member positionable alongside the lateral strut member of the knee. In such two(2) strut member embodiments of the invention only one of the strut member hinges need be biased to the extended non-bent position, while the other hinge may be a non-biased simple hinge. An upper leg engaging member is connected to the upper end(s) of the strut member(s) for anchoring the appliance to the patient's leg, above the knee. A lower leg engaging member is connected to the lower end(s) of the strut member(s) for anchoring the appliance to the patient's leg below the knee.

In accordance with the invention, the upper leg engaging component and/or lower leg engaging component of the appliance may be constructed of a generally rigid inner core member fully surrounded and encased by a soft outer cushioning material such as flexible plastic foam. In such embodiments, the upper and lower leg engaging components may be manufactured by a molding process whereby a rigid inner core member (e.g., bendable metal) is inserted into a mold and a quantity of generally flexible plastic foam is foamed onto and around said rigid inner core member so as to form a composite structure wherein said inner core member is fully surrounded and encased by the cushioning outer foam material. In such embodiments, the rigid core member of the upper leg engaging component may be generally U-shaped or semi-circular so as to extend at least partially around the thigh of the patient. The rigid core member of the lower leg engaging component may be generally L-shaped so as to extend downwardly behind the posterior aspect of the calf, around the heel and beneath the plantar surface of the foot of the patient. In such embodiments, the rigid inner core members may be formed of bendable material (e.g., bendable metal) so as to render the upper and lower leg engaging members bendably adjustable to conform anatomical and size variations of each patient.

Further in accordance with the invention, there is provided an appliance for maintaining the knee of a patient in an extended, non-bent position wherein said appliance incorporates at least one lower leg member which extends beneath the plantar surface of the foot such that abutment of the member against the plantar surface of the foot will prevent the appliance from shifting or sliding in an upward (superior) direction. Additionally, a foot attachment member (e.g., a strap) may be provided to attach the foot to the under-foot member so as to further prevent the appliance from shifting in the downward (inferior) direction. The provision of such under-foot member as a portion of the knee-extending appliance serves to maintain proper positioning of the appliance without the need for excessively tight strapping or other attachment of the appliance to the thigh or lower leg of the patient. Additionally, in such embodiments of the invention, the lower leg engaging component of the appliance may be detachable from the upper knee-extending component(s) of the appliance and separately useable as an ankle-foot orthosis for preventing foot-drop or other degenerative changes in the ankle and/or foot of the patient.

Still further in accordance with the invention, there is provided a knee-extending orthotic appliance which comprises a lower foot-ankle engaging component substantially of the configuration described in U.S. Pat. No. 5,020,523 (Bodine) entitled FOOT AND LEG SPLINT DEVICE coupled with an upper knee-extending component for urging the knee joint of the patient to an extended, non-bent position while also permitting the knee-joint to be volitionally bent when the patient so desires. In accordance with this aspect of the invention, the entire disclosure of U.S. Pat. No. 5,020,523 (Bodine) FOOT AND LEG SPLIT DEVICE is expressly incorporated herein by reference.

Further objects, advantages and aspects of the invention will become apparent to those skilled in the art upon reading and understanding the following detailed description of a preferred embodiment and consideration of the accompanying drawings.

BRIEF DESCRIPTION OF THE DRAWINGS

FIG. 1 is a perspective view of the knee extending orthotic appliance of the present invention installed upon a patient's leg;

FIG. 2 is a perspective view of the front and left side of the knee extending orthotic appliance of FIG. 1;

FIG. 3 is a perspective view of the rear and right side of the knee extending orthotic appliance of FIG. 1;

FIG. 4 is a perspective view of the knee extending orthotic appliance of FIGS. 1-3 with the foot splint portion separated therefrom and showing the front and left sides thereof;

FIG. 5 is a perspective view of the knee extending orthotic appliance of FIGS. 1-3 with the foot splint portion separated therefrom and showing the rear and right sides thereof;

DETAILED DESCRIPTION OF THE PREFERRED EMBODIMENT

Figure 6:
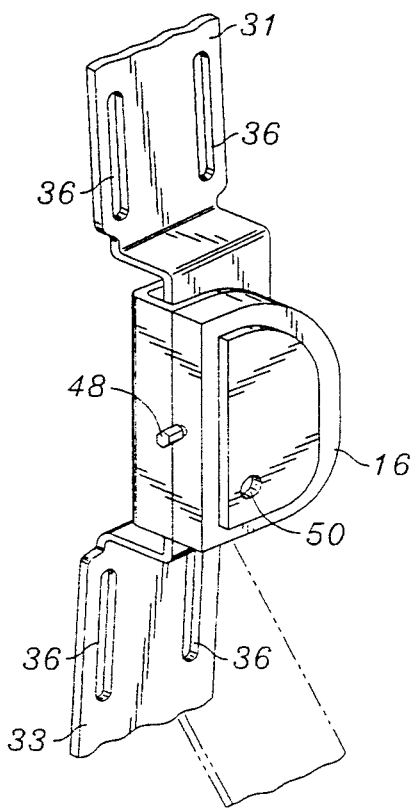
FIG. 6 is an enlarged perspective view of the spring hinge showing the outboard or front thereof.

The detailed description set forth below and in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The knee extending orthotic appliance of the present invention is illustrated in FIGS. 1-8, which depict a presently preferred embodiment of the invention. Referring now to FIGS. 1-3, the knee extending orthotic appliance is comprised generally of an upper knee-extending component 10 and a lower foot abutting component 14. The upper knee-extending component comprises medial and lateral strut members 31, 32, 33 & 34 which extend longitudinally adjacent the medial and lateral aspects of the knee and which incorporate medial and lateral hinges 16, 35 to permit bending of the knee. The lateral hinge 16 comprises a spring hinge which is spring biased to a straight non-bent configuration. One example of such spring hinge is that marketed by Bio-Tech, Inc. of Malvern, Pa. as a component of the Ultraflex TM Dynamic Splint System line of prefabricated splints.

The upper strut members 31, 32 are connectable to an upper leg collar or attachment member 18. Such upper leg collar or attachment member 18 partially surrounds the upper leg, preferably immediately above the knee. Such upper leg collar or attachment member 18 may be formed of soft, flexible material and, in one mode of construction, may comprise a generally semi-circular or U-shaped rigid insert member 39 made of rigid material such as bendable metal covered or enveloped in an outer shell or casing of cushioning material such as flexible plastic foam to form the collar or attachment member 18. Velcro TM attachment tabs 40, or other connecting members, may be positioned on the medial and lateral aspects of the outer surface of the upper leg collar or attachment member 18 so as to permit connection/disconnection of the inner aspects of the upper strut members 31, 32, thereto. Straps 21, 22 may then be passed around the outer surface of the attachment member 18 to hold the upper leg collar securely around the thigh, immediately above the knee. As more full described herein, it is generally adequate to lightly tighten straps 21 and 22 so as not to cause extreme compression of the upper leg collar or attachment member 18 against the upper leg of the patient.

The lower foot-abutting component 14 is substantially the same as the foot and ankle orthotic device described in U.S. Pat. No. 5,020,523, the entire disclosure of which is expressly incorporated herein by reference. The lower foot-abutting component 14 of the present invention may differ from the foot and ankle orthotic apparatus described in U.S. Pat. No. 5,020,523 in that the calf abutting portion of the device may be extended to wrap partially around the medial and lateral aspects of the lower leg, thereby providing support and attachment surfaces to which the lower strut members 33, 34 may be connected.

In a fashion similar to that described above with respect to the upper leg collar or attachment member 18, the lower foot-abutting component 14 may be formed of a generally L-Shaped rigid inner core member 35 surrounded or encased in cushioning material such as flexible or semi-flexible plastic foam. The rigid core member 35 may be formed of bendable metal so as to be bendable for purposes of adjusting and conforming the shape of the lower foot-abutting component 14 to the anatomical contours of the lower leg heel and foot of the patient.

The foot-abutting component 14 comprises plantar or basal under-foot portion 30 having adjustable foot attachment strap 26 extending therefrom for connection to the foot in such manner as to prevent or restrict downward (i.e., inferior) slippage or movement of the appliance. A lower leg abutting portion 28 extends upwardly behind or next to the calf of the lower leg and is connectable to the lower strut member 33, 34 by way of hook and loop connectors 42, 46.

Each of the front 21 and rear 22 upper leg straps are attached to left 31 and right 32 upper rigid members and each of the front 23 and rear 24 lower leg straps are similarly attached to the left 33 and right 34 lower leg rigid members via slots 36. The left upper rigid member is inter-connected with the left lower leg rigid member 33 via spring hinge 16 and the right upper leg rigid member 32 is interconnected with the right lower leg rigid member 34 via pivot pin 35. Optionally, the pivot pin 35 may replaced with a second spring hinge analogous to the first spring hinge 16, if desired.

Referring now to FIGS. 4 and 5, the foot abutting component 14 and lower leg band 20 are detachable from the lower strut members 34, 36 such that the foot abutting component 14 and lower band 26 used as a separate orthotic device for the treatment and prevention of foot drop and for other therapies involving the lower leg, ankle, and/or foot as described in U.S. Pat. No. 5,020,523 which is expressly incorporated herein by reference. The foot abutting component 14 and lower leg band 20 are detached from the remainder of the knee extending orthotic appliance by first detaching front 23 and rear 24 lower leg straps and then separating first 42 velcro members formed upon the lower leg band 20 from complimentary second velcro members 46 formed upon the left 33 and right 34 lower leg rigid members. Similar velcro members 40 are formed upon the upper leg band and mate with corresponding hook and loop connector material (e.g., Velcro TM) members 44 and left 31 and right 32 upper rigid members to attach the upper leg band 18 to the left 31 and right 32 upper rigid members.

Figure 7:
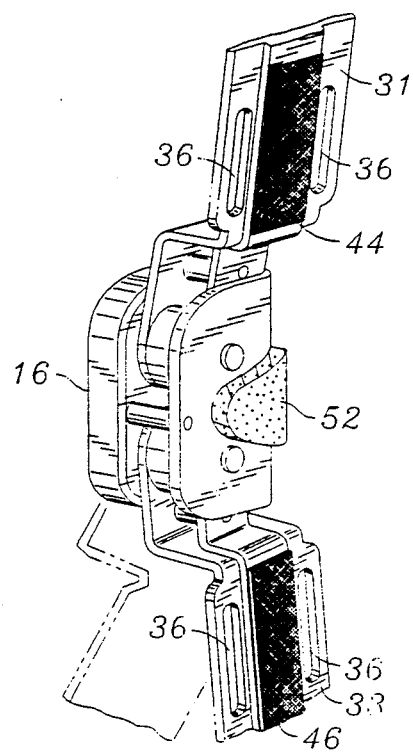
FIG. 7 is an enlarged perspective view of the spring hinge showing the inboard or rear thereof.

Referring now to FIGS. 6 and 7, the spring hinge 16 preferably has tension adjustment means 48 and tension indicator window 50 formed therein such that the tension thereof may be varied and monitored as desired.

Figure 8:
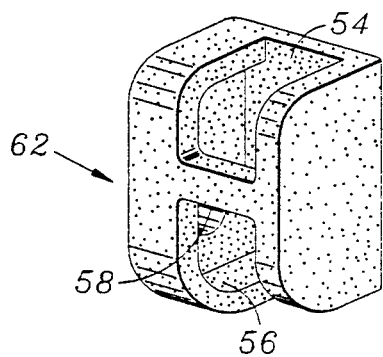
FIG. 8 is an enlarged perspective view of the foam pad or spring hinge cover.

Referring now to FIG. 8, a resilient pad or covering 52 substantially covers spring hinge 16 to prevent abrasion and to improve the comfort of wearing the knee extending orthotic appliance of the present invention.

Slots 54 and 56 formed in the covering 52 receive upper 31 and lower 33 struts or rigid members, respectively. Window 58 formed in covering 52 facilitates access to tension adjustment 48 and a similar window 59 (shown in FIGS. 2 and 4) facilitates viewing of the tension indicator 50.

A PREFERRED METHOD OF MANUFACTURE

As may be appreciated from the showing of FIG. 5, the presently preferred embodiment of the invention may be manufactured by a foamed-in-place molding process whereby the upper leg collar or attachment member 18 and/or the lower leg component 14 are prepared by molding or foaming a pliable or flexible foam cover over a pre-positioned inner core member 35 or 39. To facilitate such manufacturing process, one or more slots or apertures may be formed in the rigid core members 35, 39 to permit flow therethrough of the foaming material and, after curing of the foam, to facilitate interlocking and holding of the rigid insert member 35, 39 within the respective upper leg component 18 or lower leg component 14. It is preferred that the flexible foam cover fully encase or envelope the core member 35, 39 so that no portion of the core member 35, 39 remains exposed and so that the entire exterior surface of the upper leg component 18 and lower leg component 14 is covered by soft pliable material so as to minimize a likelihood to the patient.

The rigid inner core members 35, 39, shown by dotted lines on FIG. 5, may be formed if any suitable material such as plastic or metal. In the presently preferred embodiments, the rigid inner core members 35, 39 are formed of bendable aluminum. Such bendable aluminum inner core members 35, 39 are then placed in a mold and subsequently a flexible or pliable plastic foam is foamed therearound so as to form the desired encasement or enveloping of the rigid inner core members 35, 39. The thickness of the flexible or pliable foam surrounding or encasing the rigid inner core members 35, 39 is preferably such that it will provide sufficient cushioning to prevent injury to the patient while, at the same time, forming the desired structural body of the upper leg component 18 or lower leg 14 respectively.

It is understood that the exemplary knee extending orthotic appliance described herein and shown in the drawings represents only a presently preferred embodiment of the invention. Indeed, various modifications and additions may be made to such embodiment without departing from the spirit and scope of the invention. For example, various means i.e., ties, buckles, et cetera, may be utilized in place of front 21 and rear 22 upper straps and front 23 and rear 24 lower straps to effect attachment of the upper attachment member 10 and lower attachment member 12 to the patient's upper and lower legs, respectively. Likewise, various means other than adjustable strap 26 may likewise be utilized to foot attachment member 14 to a patient's foot. Indeed, the foot attachment member may be configured as a shoe or the like of affect attachment thereof. Thus, these and other modifications and additions may be obvious to those skilled in the art and may be implemented to adapt the present invention for use in a variety of different applications.

What is claimed is:

1. An appliance for urging the knee joint of a human being to an extended non-bent position, said appliance comprising:
   at least one elongate strut member having an upper end, a lower end and a hinge formed therebetween, said strut member being positionable adjacent the knee joint such that the upper end of said strut member extends below the knee and the hinge of said strut member is adjacent the knee to permit bending of said knee joint;
   said hinge of said at least one strut member comprising a non-adjustable spring hinge which is adapted to continually bias the upper and lower ends of the at least one strut member to an extended non-bent configuration;
   an upper-like component attachable to the upper end of said at least one strut member for anchoring the upper end of said strut member above the knee said upper leg component comprising a rigid bendable inner core member encased within and surrounded by cushioning foam material;
   a lower leg component attachable to the lower end of said at least one strut member and engageable with the leg to anchor the lower end of said strut member below the knee, said lower leg component having an under-foot portion which extends beneath the plantar surface of the foot such that abutment of the underfoot member against the plantar surface of the foot will prevent the appliance from shifting in an upward superior direction.

2. The appliance of claim 1 further comprising:
   means for attaching said underfoot member to said foot, thereby preventing said appliance from substantial movement in the downward inferior direction.

3. The appliance of claim 2 wherein said means for attaching said underfoot member to said foot comprises a strap.

4. The appliance of claim 1 wherein said lower leg component comprises a foot and ankle orthotic component comprising:
   a generally L-shaped rigid core member, said core member having a heel portion, a generally horizontal basal portion extending frontally from said heel portion, and a generally vertical portion extending upwardly from said heel portion; and
   a soft cushioning outer cover disposed on and fully surrounding inner core member in a manner as to form a body of a splint device which is positionable against the lower leg, heel, and plantar surface of the foot.

5. The apparatus of claim 4 further comprising:
   an extension member attachable to an extendable frontally from said underfoot member to hold a blanket in spaced relation above the patient's toes.

6. The appliance of claim 4 wherein said lower leg component is further configured so as to extend at least partially around the medial and lateral aspects of the lower leg to thereby provide medial and lateral attachment points to which the lower end of said at least one strut member may be attached.

7. The appliance of claim 1 wherein said upper leg component comprises:
   a generally U-shaped inner core member; and
   a cover disposed on and fully surrounding said generally U-shape inner core member, thereby forming a collar member which is positionable at least partially around the thigh of the patient.

8. The appliance of claim 7 wherein said collar is configured to extend around the medial and lateral aspects of the thigh to thereby provide medial and lateral attachment points to which the upper end of said at least one strut may be attached.

9. The appliance of claim 1 wherein said spring hinge is adjustable such that the amount of tension urging the knee to the extended non-bent position may be varied.

10. The appliance of claim 1 comprising a lateral strut member positioned longitudinally adjacent the lateral aspect of the knee and a medial strut member positioned longitudinally adjacent the medial aspect of the knee, each of said strut members having an upper end extending above the knee, a lower end extending below the knee and a hinge adjacent the knee to permit bending of the knee joint.

11. The appliance claim 10 wherein only one of said medial and lateral strut members has a hinge which is spring biased to the extended non-bent configuration.

12. The appliance of claim 1 wherein said spring hinge is encased in a soft outer cover.

13. The appliance of claim 4 wherein said soft cushioning outer cover disposed on and fully surrounding said generally L-shaped inner core member comprises flexible foam.

14. The appliance of claim 7 wherein said soft cushioning outer cover disposed on and fully surrounding said generally U-shaped inner core member comprises flexible foam.

15. An orthotic appliance for maintaining the knee joint of a human being in an extended, non-bent position, said appliance comprising:
   medial and lateral elongate strut members positionable longitudinally adjacent the medial and lateral aspects of the knee, each said strut member having an upper end extending above the knee, a lower end extending below the knee and a hinge formed therein to permit bending of the knee, at least one of said hinges comprising a non-adjustable spring hinge which is adapted to continually bias the upper and lower ends of the strut members to an extended, non-bent configuration;
   an upper leg engaging member attached to the upper ends of said strut members and comprising a rigid inner core member encased within and surrounded by a soft cushioning outer material, said upper leg engaging member being configured and constructed to effect attachment and anchoring of the appliance above the knee;
   a lower leg engaging member attached to the lower ends of said strut members and comprising a rigid inner core member encased within and surrounded by a soft cushioning material, said lower leg engaging member being configured and constructed to effect attachment and anchoring of the appliance below the knee.

16. The orthotic appliance of claim 15 wherein the rigid inner core of said upper leg engaging member comprises bendable metal which may be bendably configured to conform to variations in size and anatomy of the patient's leg.

17. The orthotic appliance of claim 15 wherein said upper leg engaging member comprises a semi-circular collar configured to be disposable at least partially around the leg and having attachment straps for tightening said collar about said leg.

18. The appliance of claim 15 wherein the rigid core of said lower leg engaging member comprises bendable metal which may be bendably adjusted to conform to variations in size and anatomical configuration of the patient.

19. The appliance of claim 15 where said lower leg engaging member comprises a generally vertical portion which is positionable adjacent the lower leg and ankle and a generally horizontal portion which extends beneath the plantar surface of the foot.

20. The appliance of claim 19 further comprising means for attaching said generally horizontal underfoot portion of said lower leg engaging member to said foot, thereby preventing the appliance from shifting in a downward inferior direction.

21. The appliance of claim 15 wherein said soft cushioning material surrounding said upper leg engaging member comprises flexible plastic foam.

22. The appliance of claim 15 wherein said soft cushioning material which surrounds said lower leg engaging member comprises flexible plastic foam.

* * * * *